US00PP20049P2

(12) United States Plant Patent
Farrow

(10) Patent No.: US PP20,049 P2
(45) Date of Patent: Jun. 2, 2009

(54) ***ILEX* PLANT NAMED 'FARROWONE'**

(50) Latin Name: *Ilex crenata*
Varietal Denomination: Farrowone

(75) Inventor: Michael W. Farrow, Earleville, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/011,390

(22) Filed: Jan. 25, 2008

(51) Int. Cl.
*A01H 5/00* (2006.01)

(52) U.S. Cl. ..... Plt./247
(58) Field of Classification Search ..... Plt./247
See application file for complete search history.

*Primary Examiner*—Annette H Para
(74) *Attorney, Agent, or Firm*—C. A. Whealy

(57) ABSTRACT

A new and distinct cultivar of *Ilex* plant named 'Farrowone', characterized by its upright and narrowly pyramidal plant form; freely branching habit; dense and bushy growth habit; relatively flat leaves; glossy and dark green-colored foliage; and good garden performance.

1 Drawing Sheet

Figure 1:
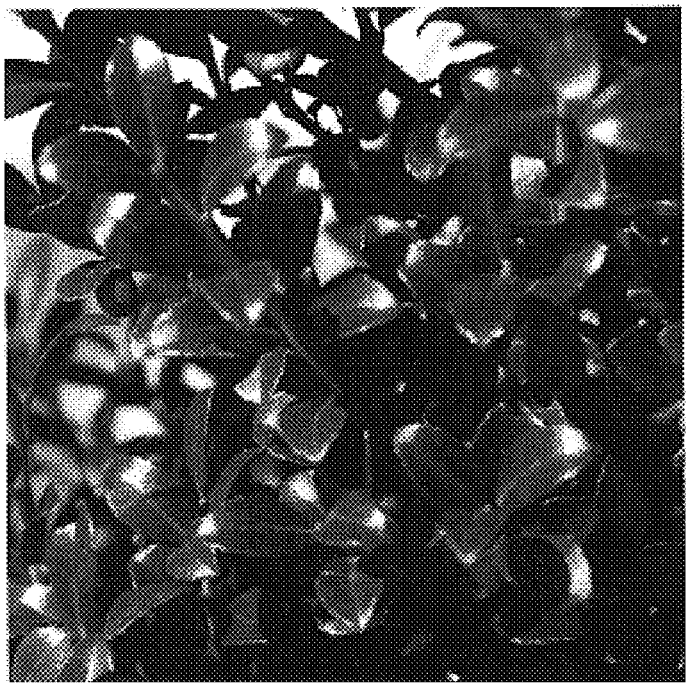
Figure 2:
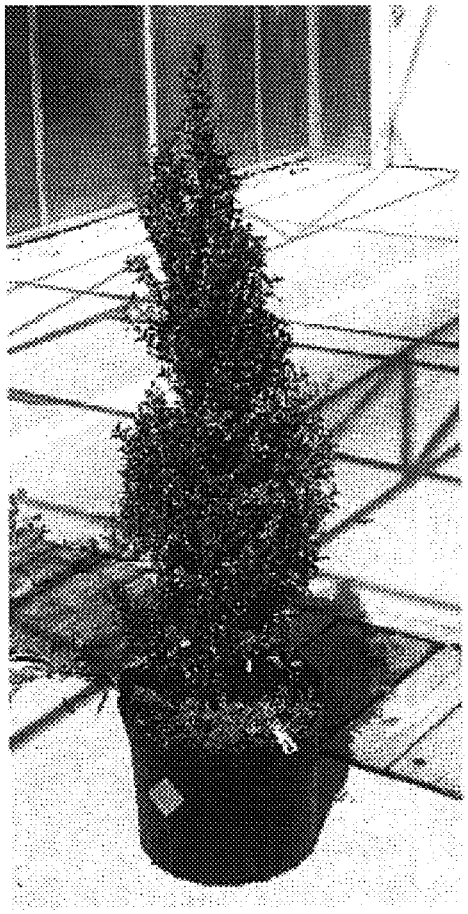

Botanical designation: *Ilex crenata.*
Cultivar denomination: 'Farrowone'.

BACKGROUND OF THE INVENTION

The present Invention relates to a new and distinct cultivar of *Ilex,* botanically known as *Ilex crenata,* and hereinafter referred to by the name 'Farrowone'.

The new *Ilex* originated from an open-pollination during the spring of 1999 of the *Ilex crenata* cultivar Sky Pencil, not patented, as the female, or seed, parent with an unidentified selection of *Ilex crenata,* as the male, or pollen, parent. The cultivar Farrowone was discovered and selected by the Inventor during the summer of 2002 as a single plant within the progeny of the stated open-pollination in a controlled environment in Earleville, Md.

Asexual reproduction of the new cultivar by hardwood cuttings in Earleville, Md. since the autumn of 2002 has shown that the unique features of this new *Ilex* plant are stable and reproduced true to type in successive generations of asexual reproduction.

SUMMARY OF THE INVENTION

The new *Ilex* has not been observed under all possible environmental conditions. The phenotype may vary somewhat with variations in environment such as temperature and/or light intensity without, however, any variance in genotype. The following traits have been repeatedly observed and are determined to be the unique characteristics of 'Farrowone'. These characteristics in combination distinguish 'Farrowone' as a new and distinct cultivar of *Ilex:*

1. Upright and narrowly pyramidal plant form.
2. Freely branching habit; dense and bushy growth habit.
3. Relatively flat leaves.
4. Glossy and dark green-colored foliage.
5. Good garden performance.

Plants of the new *Ilex* differ from plants of the parent, the cultivar Sky Pencil, in the following characteristics:

1. Plants of the new *Ilex* are narrowly pyramidal in plant form whereas plants of the cultivar Sky Pencil are narrowly columnar in plant form.
2. Plants of the new *Ilex* are taller and more vigorous than plants of the cultivar Sky Pencil.
3. Plants of the new *Ilex* have flatter and darker green-colored leaves than plants of the cultivar Sky Pencil.

Plants of the new *Ilex* can be compared to the plants of the *Ilex crenata* cultivar Steeds, not patented. In side-by-side comparisons conducted in Grand Haven, Mich. plants of the new *Ilex* differed from plants of the cultivar Steeds in the following characteristics:

1. Plants of the new *Ilex* were narrower than plants of the cultivar Steeds.
2. Plants of the new *Ilex* were taller and more vigorous than plants of the cultivar Steeds.
3. Plants of the new *Ilex* had longer, glossier and darker green-colored leaves than plants of the cultivar Steeds.

BRIEF DESCRIPTION OF THE PHOTOGRAPHS

The accompanying colored photographs illustrate the overall appearance of the new *Ilex.* These photographs show the colors as true as it is reasonably possible to obtain in colored reproductions of this type. Colors in the photographs may differ slightly from the color values cited in the detailed botanical description, which accurately describe the colors of the new *Ilex.*

The photograph at the bottom of the sheet comprises a side perspective view of a typical plant of 'Farrowone' grown in a container.

The photograph at the top of the sheet is a close-up view of typical leaves of 'Farrowone'.

DETAILED BOTANICAL DESCRIPTION

The aforementioned photographs and following observations and measurements describe plants grown in Grand Haven, Mich. in three-gallon containers, in an outdoor nursery during the spring and summer and under commercial production conditions. Plants used for the photographs and description were about four years old. In the following description, color references are made to The Royal Horticultural Society Colour Chart, 2001 Edition, except where general terms of ordinary dictionary significance are used.

Botanical classification: *Ilex crenata* 'Farrowone'.

Parentage:

*Female, or seed, parent.*—*Ilex crenata* cultivar Sky Pencil, not patented.

*Male, or pollen, parent.*—Unidentified selection of *Ilex crenata,* not patented.

Propagation:

*Type.*—By hardwood cuttings.

*Time to initiate roots, winter.*—About 40 days at temperatures of 20° C.

*Time to produce a rooted young plant, summer.*—About four months at temperatures of 20° C.

*Root description.*—Fine, fibrous.

*Rooting habit.*—Freely branching; dense.

Plant description:

*Plant form and growth habit.*—Perennial evergreen shrub; upright and narrowly pyramidal plant form. Vigorous growth habit.

*Branching habit.*—Freely branching habit; dense and bushy growth habit with numerous lateral branches developing per plant.

*Plant height.*—About 85 cm.

*Plant diameter, area of spread.*—About 30 cm.

*Lateral branch description.*—Length: About 24 cm. Diameter: About 3 mm. Internode length: About 5 mm. Strength: Strong. Texture: Smooth, glabrous. Color, young stems: 146C. Color, mature stems: 148A.

*Foliage description.*—Arrangement: Alternate, simple. Length: About 2.5 cm. Width: About 9 mm. Shape: Narrowly elliptic. Apex: Narrowly acute. Base: Cuneate. Margin: Slightly serrulate. Venation pattern: Pinnate. Texture, upper and lower surfaces: Smooth, glabrous; thick, leathery, rugose. Aspect: Relatively flat. Color: Developing foliage, upper surface: 143A. Developing foliage, lower surface: 143B. Fully expanded foliage, upper surface: 139A; venation, 139A. Fully expanded foliage, lower surface: 139B; venation, 139B. Petiole: Length: About 3 mm. Diameter: About 1 mm. Texture, upper and lower surfaces: Smooth, glabrous. Color, upper surface: Close to 139A. Color, lower surface: Close to 139B.

Flower description: A description of the flowers is not available to date as flower development has not been observed on plants of the new *Ilex*.

Garden performance:

Plants of the new *Ilex* have been observed to have good garden performance and to be tolerant to rain, wind and temperatures ranging from about −20° C. to about 30° C.

Disease/pest resistance: Plants have not been observed to be resistant to pathogens and pests common to *Ilex*.

It is claimed:

1. A new and distinct cultivar of *Ilex* plant named 'Farrowone' as illustrated and described.

* * * * *